United States Patent [19]

Rolfo-Fontana

[11] 4,062,652

[45] Dec. 13, 1977

[54] REAGENT UNIT INTENDED FOR MICROANALYSES OF STANDARD TYPE AND DEVICE AND METHOD FOR ITS PRODUCTION

[76] Inventor: Gudrun Birgitta Margareta Rolfo-Fontana, 20, Boulevard des Moulins, Monte Carlo, Monaco

[21] Appl. No.: 483,652

[22] Filed: June 27, 1974

[30] Foreign Application Priority Data

Feb. 7, 1974 Sweden .................................. 7401658

[51] Int. Cl.² .................... B01L 11/00; B65D 23/04; B65H 1/08; G01N 33/00

[52] U.S. Cl. ............................ 23/253 R; 23/253 TP; 23/259; 23/292; 141/1; 141/98; 141/130; 195/127; 206/818; 215/1 C; 221/279; 366/273

[58] Field of Search ............... 23/253 R, 253 TP, 259, 23/292; 215/1 C, 1 R; 206/818, 350, 219; 221/279, 280, 226; 195/127

[56] References Cited

U.S. PATENT DOCUMENTS

| | | | |
|---|---|---|---|
| 1,638,181 | 8/1927 | Bell ....................................... | 221/279 |
| 2,383,098 | 8/1945 | Wheaton, Jr. ...................... | 215/1 R X |
| 2,600,589 | 6/1952 | Swanson ........................... | 206/350 X |
| 3,489,521 | 1/1970 | Buckle et al. ...................... | 23/253 R |
| 3,508,587 | 4/1970 | Mauch ............................... | 215/1 R X |
| 3,526,480 | 9/1970 | Findl et al. ........................ | 23/253 TP |
| 3,545,934 | 12/1970 | Dryden et al. .................... | 23/253 R |
| 3,650,698 | 3/1972 | Adler ................................. | 23/253 TP X |
| 3,663,374 | 5/1972 | Moyer et al. ..................... | 23/253 TP UX |
| 3,728,081 | 4/1973 | Bidanset ........................... | 23/253 R X |
| 3,843,450 | 10/1974 | Saxholm ........................... | 23/253 R X |
| 3,859,050 | 1/1975 | Horn et al. ....................... | 23/253 R |
| 3,897,216 | 7/1975 | Jones ................................ | 23/253 R X |

Primary Examiner—Joseph Scovronek

[57] ABSTRACT

A prefabricated micro-quantity reagent dosage unit for an analytical procedure, is provided involving reaction of a chemical reagent with a reaction mixture to be analyzed. The unit comprises a composite structure which incorporates the chemical reagent and includes carrier means for carrying the chemical reagent and magnetizable material to facilitate handling of the carrier means and for effecting movement of the latter, under action of a magnetic field acting on the magnetizable material, when the carrier means is subjected to the reaction mixture. The carrier means is provided with precise micro-quantities of reagent preparatory to a single analysis and by virtue of the magnetizable material the composite structure may readily be handled for storage under conditions favorable for the durability of the reagent, simultaneously enabling transfer of the composite structure to the reaction mixture without risk of contamination of the latter.

6 Claims, 6 Drawing Figures

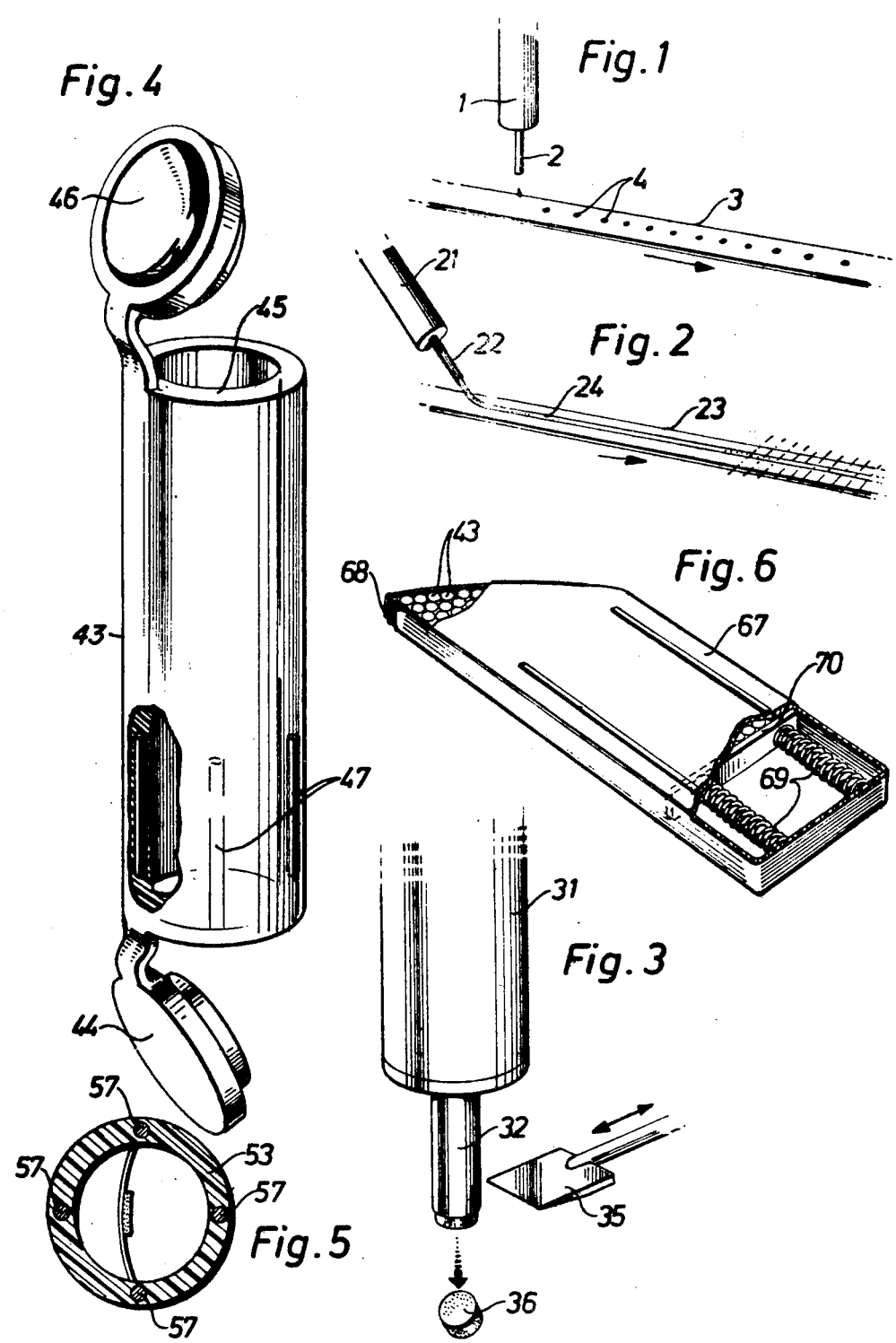

REAGENT UNIT INTENDED FOR MICROANALYSES OF STANDARD TYPE AND DEVICE AND METHOD FOR ITS PRODUCTION

The invention relates to a preferentially prefabricated reagent unit for microanalyses of standard type, to apparatus for production of such reagent units and to a method for such production. By virtue of the invention, precisely measured reagent doses are available before the analytic procedure for qualitative and quantitative microanalyses of very small quantities of substances.

Generally speaking the chemical analysis for establishment of the nature and quantity of constituents in a substance (sample material in a reaction mixture) using chemical or physico-chemical methods, especially with microanalysis, has an extremely great practical significance, especially for diagnostic use within medicine (on, inter alia, blood and urine samples) but also within public health and environmental protection, for food inspection, within agriculture and within the chemical industry, especially the pharmaceutical industry, apart from the purely general significance for chemical laboratory work.

In such an analysis one makes use of every observable property of the element the occurrence of which in a given substance is to be established. It is primarily a question of the mode of reaction of the element, i.e. whether one can produce with it, for example, a colour which can be measured or whether the concentration of the element can be established through its catalytic (e.g. enzymatic) effect. But in addition the colour, for example, of the element itself can be determined, or its solubility, density, electrical conductivity, emission and absorption of light, the effect on it of polarized light, its refraction index, crystal structure, atomic configuration etc. The number of possible methods of analysis in each particular case is thus dependent on the number of such properties of the element.

The kinds of analysis which may be of interest are dependent, apart from the sample material, also on the intention of the analysis.

Of most interest in conjunction with the invention are so-called wet chemical analysis methods, i.e. methods in which chemical reactions are performed in solutions.

Sample and reagent are in this case treated by means of volume measurements, i.e. with pipettes, burettes and other measuring vessels. The event in the solution can then be followed by different methods, such as photometric, spectrophotometric, fluorimetric, turbidimetric, nephelometric, polarimetric or other optical methods. These are the commonest methods for clinical analysis.

There is, however, a great need for exact volumes of reagent also for electrochemical analysis methods, e.g. methods in which one uses specific ion electrodes or measures electrical conductivity, or methods such as polarography and electrometrical titrations.

Also for the serological methods, especially important for medicine, in which for example, one wishes to find the agglutinizing capacity of blood corpuscles or precipitation of antigen - antibody aggregates, one can use reagent unit doses. Certain bacteriological analyses are also dependent on an exactly dispensed reagent.

For all the aforementioned kinds of analysis the usual procedure at present is to use reagents in the form of solutions, the reagent solution being added by pipetting in the course of the analysis.

The addition of a precise quantity of reagent solution to the investigated substance is critical to the accuracy of the analytical determination. As a result of the increasing automation of laboratory work in recent years it is desirable to limit the number of samplings on patients and to subject the samples taken to increasing numbers of analyses. This has the result that the quantity of substance available for each analysis becomes increasingly smaller. Consequently the quantity also of reagent solution added to each sample must also be dispensed and measured in increasingly small volumes to obtain satisfactory accuracy. Using the current pipetting procedures which dispense the reagent during the analytic procedure one can at present, by automatic technique, measure and dispense liquid volumes down to about 30 $\mu$l within an error of below $\pm$ 1%.

It has been considered impossible to come below these figures with conventional devices, owing to the capillary effect, drops at the tip of the pipette, small leakages etc.

The present invention is intended to facilitate especially microanalyses of standard type and to refine the results of these analyses by providing in accordance with the invention a prefabricated micro-quantity reagent dosage unit for use in the course of an analytical procedure involving reaction of a chemical reagent with a reaction mixture to be analyzed, said unit comprising a chemical reagent of predetermined volume, carrier means for carrying said chemical reagent of predetermined volume and a magnetizable material contained by said carrier means to facilitate handling of said carrier means and for effecting movement of the carrier means, and the reagent carried thereby, when introduced into said reaction mixture, said carrier means, said reagent and said magnetizable material comprising a composite structure adapted for storage, transfer and use in a single analytical procedure under action of magnetic forces adapted to be applied to said magnetizable material. The carrier means by virtue of the magnetizable material allows handling of the microunit dose and its storage under conditions favourable for the durability of the reagent and permits transfer of the reagent from the dispensing device to the reaction solution without risk of contamination of the latter. By virtue of being prefabricated, the dosage unit of the invention provides exact and reproducible quantities of the dose and permits agitation of the reaction solution since the carrier, as noted, can be moved in said solution.

The adhesive material may have the form, for example, of one or more wires or cylinders in the longitudinal direction of the carrier, for example in the wall of a tubular carrier.

According to a further development of the invention the reagent is bound to the carrier through the fact that the former consists of a strongly concentrated solution or of a wholly or partially solid substance which may have been produced through the fact that the reagent contains inert elements with a viscosity-raising effect such as agar-agar, pectins, gelatin or cellulose derivatives and/or that the reagent is bound to the carrier since the reagent exists in solid form produced by lowering of its temperature. The reagent may thus contain inert substances with viscosity raising effect, e.g., agar-agar, pectus, gelatin or cellulose derivatives.

The reagent dose can be situated either within a limited area on a carrier of band form, for example a plastic strip, or may consist of an exactly cut length of a wire or bead of reagent on such a carrier. The reagent unit may also consist of a reagent-containing carrier in the form of a tubular element, possibly also with a narrow channel in the wall to take sample substance (for example blood serum), for example a plastic tube with end seals.

The invention also relates to apparatus for production of reagent units of the aforesaid kind which contains a syringe pipette driven, for example, by a synchronous motor and furnished with a plunger, the pipette — under action of the plunger — delivering the reagent intended for dispensation into or onto a reception unit, i.e. carrier means moving uniformly in a path past the mouth of the syringe pipette, the reception unit taking the reagent either, for example, as a bead on a band containing a magnetic material or as quantities of reagent fed out in unit doses directly onto such a band, or as quantities of reagent fed out directly into tubular carrier elements containing magnetic material and movable in line in the path.

The apparatus may be such that the reagent dose expelled at the point of the pipette in highly viscous or gelatinous form is separated from the point of the pipette by a knife-edge or a sharp edge, for example the edge of a tubular carrier passing said tip.

The invention also relates to a method for production of said reagent unit, the reagent first being fed out by a syringe pipette, for example driven by a synchronous motor and furnished with a plunger, onto the reception unit movable uniformly in a path past the mouth of the syringe pipette, the reception unit taking the reagent either as a bead on a band containing a magnetic material or as reagent fed out in unit or discrete doses on such band, or as quantities of reagent fed out in unit doses directly onto tubular carrier elements containing magnetic material and movable in the path, and finally, in the two first-named cases, the band, possibly after drying or freezing of the reagent, being cut into carrier elements having exact unit doses or, in the latter case, the individual tubular carrier elements being sealed.

The invention will be apparent from the subsequent description, as also from examples of reagents and analyses, and with reference to the attached drawing, where FIG. 1, 2 and 3 show different methods of manufacturing reagent units, FIG. 4, 5 show examples of reagent units with tubular carriers and FIG. 6 shows a number of reagent units combined into a casette.

The invention will also appear from the claims following the desdription.

The factors which limit the accuracy in conventional pipetting are lack of exactness in the delimitation of the enclosed volume of liquid reagent. An ordinary pipette consists of a rigid tube which is filled with solution in vertical position. The preciseness of the pipetting is dependent, among other factors, on the delimitations upwards (where a meniscus is formed) and downwards where the tube is drawn out to a tip to provide a sharper limit. None of the surfaces is especially well defined. Especially the lower surface can be so acted upon that the level of liquid remains at different heights on different occasions. When dispensing an enclosed volume of reagent through run-out, a certain volume inevitably remains on the wall (especially in the case of viscous solutions and quick emptying). This makes it impossible to dispense a uniform volume of reagent which is essential for precise analysis.

The present invention avoids this and other drawbacks by providing a composite structure, prepared in advance, with a precise volume of reagent for standard microanalyses (unit doses of 0.1–30 $\mu$l, i.e. of an order of 0.1–30 $\mu$g).

In principle the division into predetermined volume doses of the reagent is a troublesome procedure especially if performed during an analysis. An objective of the invention is to have available when the analysis is to be made, a composite structure having an accurately determined quantity of reagent suitable to the analysis. With previously used mechanical pipetting of the reagent, any disturbance which may arise in the course of the analysis will not only adversely affect the analysis but also a possibly expensive sample material which is difficult to replace. According to the invention this risk is eliminated. The problem of space, which is also significant for large analysers is also acute and due to crowding of parts the operation is difficult to supervise.

The invention involves providing small measured doses on, for example, a plastic tape which contains magnetic material or in a row of small containers of suitable size and shape, the storage of which is feasible in shaped cassettes.

The fact that, at the time of analysis, one has available the necessary reagent in exact and known quantity in unit doses, preferentially prefabricated, ensures that this exact and difficult work need not be done in the course of the analysis which will thus require only appropriate implementation in order to adapt to the use of prefabricated reagent doses of predetermined quantity.

In this way, at the time of analysis, the need for measuring or ensuring predetermined amounts of the reagent is avoided, it only being necessary to 1. handle prefabricated dosage units having a predetermined volume of reagent; and
2. increasing the viscosity of the reagent either through addition of inert substances which do not affect the analyses and/or by lowering of the temperature of the reagent.

Implicit in this proposal to alter the consistency of the solutions to high viscosity (even to gelatinous form) is the possibility that one can thereby obtain a sharper delimitation of the volume in pipetting and, by using a plunger pipette (syringe pipette), one can nevertheless avoid the disadvantage of subsequent run-off of the viscous solutions on the walls.

The pipetting procedure according to the invention for dispensing a predetermined quantity of reagent presumes such a consistency of the solution (or of the gel) that the surplus reagent at the lower tip of the pipette can be scraped off (or cut off in the case of a gel). One then obtains a sharp surface which is so definitely defined that even small volumes of reagent can be measured or dispensed with sufficient accuracy (i.e. with a mean error below 1%).

The technique used for dispensing exact volumes must be adapted to the consistency of the material dispensed. For solutions one uses, for example, drying under the tip of the pipette in order to remove an excess of reagent solution there. For viscous solutions extruded from a syringe pipette, scraping off with, for example, a Teflon edge has proved adequate. For gelatinous reagents a rotating knife, for example, is advantageous, but also other known procedures such as microtomy (in the same way as in the preparation of microscopic specimens) produce the intended result.

It should be noted that with this type of pipetting the syringe tip need not be rinsed with diluent as is the case with presently used techniques which necessitate multiple dilution often a disadvantage.

Finally it is possible 3. also to accelerate the dissolution of the reagent in a one-dose carrier in the reaction mixture.

Storage and preservation of the reagent must be adapted to the chemical characteristics in each particular case. A common feature, however, is that the reagent is subjected to a greater or lesser degree of drying. In such case, in the use of the reagent, there are certain difficulties in obtaining a rapid dissolution of the chemical element.

In principle the reagent can be preserved on flat, tubular or entirely enclosed carriers which can be gripped and handled with conventional gripping tools. For the small dimensions involved in microanalysis, however, the use of magnetic forces has proved especially valuable.

By enclosing magnetic material in the carrier one obtains a simple means of moving the reagent unit.

Equally important is also the possibility of vibrating, agitating and whisking the carrier, so that the reagent is quickly dissolved.

The process can be accelerated through chemical (hydrophilic) additions to an aqueous solution.

It is of great importance that complete dissolution takes place. In some cases the surface must be specially pretreated in order not to retain the reagent. For different cases there are several methods and substances known to facilitate complete and rapid dissolution.

With the foregoing in mind one among the many objectives of the invention is to change the viscosity and surface tension of the reagent, to permit exact measurement and dispensing of very small volumes thereof for use for individual analyses, obviating the need for the reagent to be measured or pipetted during the analysis.

The invention is accordingly — instead of further refinement of, for example, the pipetting by, among other means, additions of substances which do not affect the analysis — to so alter the characteristics (physico-chemical) of the reagent solutions that the apportionment into exact quantities is facilitated. For the use of individual doses of reagent for each analysis, accordingly, it is required that a. the reagent be supplied exact quantities prior to the analysis,
b. the doses be individually supported (by the carrier means) preserved and handled,
c. possibly the viscosity of the reagent is increased and, finally
d. the reagent, added in unit doses is dissolved and well mixed in the reaction mixture in which the chemical process takes place.

The use relates primarily to clinico-chemical analyses, but the principle can be applied wherever the analysis work warrants the adoption of preprepared doses of reagent.

The procedure must permit the dispensing of small quantities of reagent for possible use in manual and mechanized or automated analysis work. This provision of micro-dosage units with a predetermined volume of reagent is especially of advantage when using large analysis machines because it reduces the number of pipettings which is quite large.

In the sequel some general points of view will be adduced concerning the essential elements of analysis in the general routine of a chemical microanalysis in which the reagents used for addition to the reaction tubes are exactly measured and carried by individual carrier means so that they can simply and reliably be handled magnetically during the analysis.

The carrier means thus contain a predetermined quantity of reagent (unit dose) and are so designed that they can receive a small quantity of the sample to be analysed and transported to the reaction tube together with the reagent addition.

The carriers are also so designed that they can contribute to mixing of the basic solution, the sample substance and the reagent additive in the reaction tube. This is achieved according to a separate invention of patent application Ser. No. 483,621 (now U.S. Pat. No. 3,982,131) for which patents have been applied simultaneously with the present application, magnetically by providing the reaction tube with an electric coil, in addition to providing the carrier means with magnetic or magnetizable material, the field of the coil altering magnitude and/or direction by being intermittently activated with pulse-shaped or alternatively reversed electrical impulses which may be of different duration.

In the following disclosure, I will briefly discuss how the various analysis phases are conducted using reagent unit doses.

A. Sample measurement

The procedure which at present is considered to be most exact, and is therefore most used for addition of a small but exactly measured volume of the sample material intended for analysis, is carried out with a so-called dilutor. For this purpose the desired volume is suctioned up into a narrow tube, appropriately of hydrophobic plastic, and the sample is later extruded with a specific quantity of diluent liquid which at the same time flushes the tube clean for new use. This procedure presumes that a considerable dilution is always effected, which sometimes is very advantageous, and that the time is extended, since the dispensing of sample must await the addition of diluent.

The invention permits the measurement of the sample without the need to add another liquid. For the actual sample measurement there are three alternatives available depending on the size of the sample.

For the largest volumes, more than 30 $\mu l$; an injection syringe is used, filled for example with blood serum and so arranged that predetermined quantities are dispensed for each analysis.

For a smaller volume the sample is suctioned up into a thin-walled plastic tube cut into lengths which correspond to the desired volumes for different analyses.

For the very smallest quantities it is necessary, with a screw type pipette, to press out the insignificant sample volume and then either scrape off the part of a drop which has emerged and is suspended under the tip or cut it off with a sharp edge after carbon dioxide freezing, so preventing the spread of sample liquid which otherwise lowers the precision and reproducibility.

B. Addition of reaction to the reagent tubes apart from what may exist in the quantity of liquid constituting the basic solution.

Transfer of the sample to the reaction tube is done with the carrier body of the reagent together with the reagent.

Reagents of considerable volume, i.e. more than 50 μl, and in liquid form, are added with a conventional syringe pipette of the type which has a reversing valve which, on a plunger movement, discharges a specific volume of liquid in one direction and, on the reverse movement of the plunger fills the reagent into the syringe pipette from a storage vessel.

Reagents in solid form and in small quantities, which are easily and quickly soluble, as also reagents in small volumes — less than 30 μl — in ready-made carriers which contain the quantity of reagent with the necessary exactness, are so used that these additions of reagent, accordingly, follow the carrier body (without loss of substance) until it is lowered into the reaction tube which then contains the basic solution.

An essential feature is that between the sample liquid containers (syringe pipette and hose) according to the invention a carrier means is introduced which forms an intermediate step prior to the reaction tube. This prevents the contamination which otherwise may arise when the end of a hose or the tip of a pipette is dipped in a solution. This carrier, as already mentioned, can on the one hand receive the small quantity of sample, on the other hand serve as storage vessel during the transport both of sample substance and reagent to the liquid in the reaction tube, and finally have the important function of mixer in the solution since it is provided with magnetic material.

In the following examples will be given of chemicals etc. which are required for analyses and which may be used in reagent units, and of the procedure and of the various alternatives between which the laboratory may choose.

The chemicals may have amorphous or microcrystalline form in order easily to dissolve. Inert substances having a very high solubility may be added.

A. Chemical substances

DL-Alanine
4-Aminoantipyrine = 4-amino-1.5-dimethyl-2-phenyl-3-pyrazolone
2-Amino-2-methyl-1-propanol
Ammonium hepta-molybdate, 4 aq.
Ascorbic acid
Bromcresol green = 3.5', 5.5'-tetrabromo-m-cresol sulphon phthalein
Brij 35 = polyethylene lauryl alcohol
Citric acid, 1 aq.
Caffeine
O-Dianisidine = 3.3'-dimethoxybenzidine
Dextran sulphate
EDTA = ethylene diamine tetra-acetic sodium salt
Fast Red B salt = 5 nitro-2-amino-methoxybenzene diazotate, Sigma
Phenol
Phenyl phosphate di-sodium salt
Hydroquinone
HBAB = 2-(4'-hydroxybenzazo)-benzoic acid
INT = 2-(4-iodophenyl)-3-(4-nitrophenyl)-5-phenyl-tetrazolium chloride
Isopropanol = 2-propanol
Dipotassium hydrogen phosphate
Dipotassium oxalate, 1 aq.
Potassium-ferricyanide = potassium hexacyanoferrate (III)
Potassium-sodium-tartrate, 4 aq.
alpha-ketoglutamic acid = 2-oxo-glutamic acid
Copper sulphate, 5 aq.
Magnesium chloride, 6 aq.
Magnesium sulphate, 7 aq.
DL-Lactic acid, 85% by weight (DL-Lactic acid 85% W/W)
L-Lactic acid, 98–100% by weight (L-Lactic acid 98%–100% W/W)
NAD = Nicotinamide adenine dinucleotide
NADH = Reduced nicotinamide adenine dinucleotide
alpha-Naphthyl phosphate = sodium naphthyl (1) phosphate
Sodium acetate
Sodium azide
Sodium benzoate
tri-Sodium citrate, 2aq.
Sodium hydroxide
Sodium hypochlorite
Sodium carbonate
Sodium nitrite
Sodium disulphite (Na2-S2-05)
Sodium sulphite
di-Sodium tetraborate, 10 aq.
Neocuproine = 2.9-dimethyl-1, 10 phenanthroline
di-Nitrophenylhydrazine = 2.4-dinitrophenylhydrazine
Nitroprussid sodium, 2 aq. = disodium pentacyanonitrosyl ferrate
Nitroso-R = 1-nitroso-2-hydroxy-3.6-naphthaline-disodium-sulphonate
PMS = 5-methyl-phenazinium methyl sulphate
Picric acid
Sulphanilic acid
5-Sulphosalicylic acid, 2 aq.
TPTZ = 2.4.6-tri(2-pyridyl)-1.3.5-triazine
TIBC
Thymol
Zinc sulphate, 7 aq.

B. STANDARDS

1. For the preparation of primary absolute standard solutions the following examples may be given:
They require an extreme exactitude of the unity doses.
Pyruvic acid
Glucose
Ferrinitrate, 9 aq.
Calcium carbonate
Potassium dihydrogen phosphate
Potassium nitrate
Cholesterol
Creatinine
Lactic acid
NADH (reduced nicotinamide adenine dinuleotide)
Sodium nitrite
Oxaloacetic acid
Uric acid
Urea 2. Certain primary standards require control analyses. This is true with respect to the following examples:
Albumin, human and animal serum albumin
Bilirubin
Enzyme preparations, such as amylase, various esterases, glycose oxidase, peroxidases, urease, uricase
Hemoglobin derivatives such as oxihemoglobin, cyanhemoglobin
Combinations for multiple channel analyzers.

Apparatus standards and chemical mixtures for control of the apparatus function, for instance photometry (Colorimetric standard)

Standard serum preparations, commercially available with different concentrations and enzyme activities.

C. REAGENTS IN BUFFER SOLUTIONS.

A chemical reaction very much depends on the acidity and also on the ion density. The acidity, pH, is given by the relation between acidity and basicity, while the absolute amount or concentration is of minor importance within certain limits.

These reagents are often used in the basic solution. The following examples give an idea of what is used.

Citric acid/sodium hydroxide, barbital/barbital sodium, EDTA/ odium hydroxide, glycin/sodium hydroxide, primary and secondary orthophosphate of sodium or potassium salts, tris buffer base/tris buffer hydrochloride and acetic and sodium acetate.

EXAMPLES OF PROCEDURE FOR USE OF REAGENT UNIT IN CHEMICAL ANALYSIS.

EXAMPLE I

Evaluation of alternative means for determination of the creatinine content in blood serum with Jaffe's picrate reaction. The alternatives differ as regards the composition of the basic solution.

1. Basic solution, 500 μl containing alkaline picrate to which is added 40 μl blood serum. This alternative is the commonest for analyses in large series and thus especially for automation. Its main disadvantage is the poor durability of the reagent, which undergoes continuous disintegration. The need for precision determines whether the reagent must be prepared daily or several times a day. Preferably the reagent should always be newly prepared.
2. Basic solution in form of 500 μl 0.15 M NaOH to which, after mixture, is added a reagent dose of 2.3 ± 0.01 picric acid which, through effective mixing, is quickly dissolved and then reacts with the creatinine.
3. Basic solution in form af 500 μl pure water, to which, as reagent unit, is added 40 μl blood serum and 3 ± 0.015 mg NaOH. Through effective mixing the sodium hydroxide is dissolved and mixed with the serum sample. Thereafter 2.3 ± 0.01 mg picric acid is added to the reagent unit.

In all alternatives photometry is done at 560 nm wavelength and one has the choice of so-called kinetic determination, i.e. the use of the first part of the reaction time as best expression for the creatinine concentration or, by the old conventional method, reading of the formation of reddish colour after a specific, somewhat longer time, in which case, however, certain non-specific side-reactions with elements which are not creatinine are more or less included.

Evaluation Under given conditions alternatives 2 and 3 are best from the analytical point of view but require reagent units and effective mixing. The choice between 2 and 3 would probably depend on whether basic solution containing 0.15 M NaOH is used (for other analyses performed simultaneously). Practical and economical reasons would appear to favour this procedure. Pure water is a common additive.

EXAMPLE II

Determination of the enzyme activity for so-called alkaline phosphatase in blood serum.

Of various methods available for determination of this enzyme activity the choice has been to determine the quantity of phenol which is enzymatically liberated from phenyl phosphate under standardized conditions and during a given time, after which the reaction is interrupted and a red quinone is formed by chemical reaction with 4-aminoantiphyrine (AAP) and potassium ferricyanide.

The following alternatives may be considered:

1. Conventionally the method is that, to 400 ||1 of a basic solution containing a borate/carbonate buffer with magnesium addition for optimal enzyme effect and containing 0.44 ± 0.002 mg sodium phenyl phosphate as substrate, is added a quantity of 6 μl blood serum. After mixing, the enzyme is allowed to act during a specific time, after which 0.61 ± 0.006 mg AAP is added, for example in 50 μl water, and 4.8 mg potassium ferricyanide, for example in 50 μl water.
2. To a basic solution of borate/carbonate buffer with magnesium activator is added a reagent unit containing 6 μl blood serum and a quantity of 0.4 ± 0.002 mg sodium phenyl phosphate. After incubation a reagent unit is added containing 0.61 ± 0.006 mg AAP and a reagent unit containing 4.8 mg potassium ferricyanide, possibly in the same reagent unit.

In both cases the determination is made by photometry at 505 nm and the activity is indicated in units based on the quantity of phenol liberated in the reaction.

Evaluation The latter alternative is superior, as the critical reagent consists of sodium phenyl phosphate in solution and has poor durability. On the other hand the buffer solution is durable and it is advantageous to have the enzyme substrate separate and in dry form, in addition to the gain of not needing to take into account that in the analysis the pipetting will not be completely successful and exact.

From a purely general point of view it should be noted also that the method of using predispensed reagent doses often places great requirements on the exactness and it must be observed that this applies to the final quantity of reagent. Thus the durability must be taken into account and, to increase the durability, one can count on being able to preserve single doses, often dry, of reagent chemicals better than in solution.

The quantities usually involved in analyses in which the reaction volume at the final measurement is around 0.5 ml (500 μl) are about 0.5–50 mg. This implies that the absolute error may sometimes be at most 1 μg, e.g. 0.20 mg ± 0.001 mg (200 ± 1 μg).

In principle the use of prefabricated reagent units suggested that the accuracy must be attained in the manufacture instead of during its dispensing in the course of the analysis.

Common to all kinds of chemicals in reagents, and which are exemplified in groups A, B and C, is that the reagent unit must be definitely obtainable in the correct quantity at a given time.

Over and above this, however, special advantages are offered for certain kinds of chemicals. One of the most general rules is that chemicals show a greater durability in more concentrated solutions or in solid form. For the reagent unit this principle is even more utilizable than the present method of using strong "stock solutions" from which temporary preparations are made.

In some cases, when the reagent is expensive, this increased durability is especially important and better than the now common technique of making solutions and preserving them in deep-frozen state, e.g. NADH.

For all standard substances the precision of the quantity of reagent is of decisive significance (group B), which makes the durability point of view still more important.

In many cases it is advantageous to preserve reagent components separately, e.g. picric acid and NaOH for creatinine determination.

For many solutions, e.g. acetate or phosphate buffer solutions, newly prepared solutions are advantageous since they are quickly destroyed through bacterial growth. For reagent units containing, for example, the reagents referred to in group C, therefore, one needs no preservatives, even when their use would be possible without disturbing the chemical reaction.

Factory manufacture of reagent ensures not only a uniform quality but also an increased durability and better stability. The question of what additive should be used may be left aside; additives may, however, provide extremely good results. Prefabricated doses in exact quantities are thus a step in a development which, through the use of reagent units, opens up new possibilities. One can then count on identical results in different laboratories. At present - mostly due probably to small differences in, for example, the purity of water, the quality of washing etc. - different results may be obtained although the laboratories use the same methods of analysis, the same chemicals and the same type of measuring instrument. Reagent units ensure a much greater uniformity and the possibility of comparing results and finding means for correction.

The drawing shows a few examples of how a reagent unit according to the invention can be achieved.

According to FIG. 1 it is seen that the reagent, through for example a syringe pipette 1 actuated by a plunger driven by a synchronous motor, not shown in the drawing, is fed out to a carrier means or receiving unit in the form of a movable band 3, fed past the mouth 2 of the syringe pipette in the direction of the arrow P, in unit doses 4. The band may be of plastic containing magnetic material. The unit doses 4 are dried or frozen and the band is thereafter cut with a knife-edge, possibly a rotating knife, into unit doses.

A similar device is shown in FIG. 2, where by means of a similar pipette 12 with a nozzle 22 a bead 24 of the reagent is fed out on a carrier means comprising band 23. The band, which in this case as well is seen to contain magnetic material, is thereafter cut with a knife, not shown, into exact unit lengths which provide unit doses with exactly dispensed quantity of reagent.

In a third embodiment the carrier means or receiving unit is arranged for movement along a path and comprises a number of upright tubular carriers of the type shown at 43 of FIG. 4. These tubular carriers provided with end seals move either past a syringe pipette of the kind shown in FIG. 1 or of the kind 31, shown in FIG. 3. In this case the agent, which may be in gel-like form, is separated with a knife 35 which moves to and fro in the direction of the arrow, so that thin-cut slices 36 of the reagent fall down into the upright tubular carriers 43, the lower end seals cover 44 of which, during movement of the carrier along the path is closed. One may also see that, instead of a knife 35 which cuts the reagent fed out from the nozzle 32, the edge 45 of the tubular carriers can scrape off the reagent dose extruded in gelatinous form. After the individual tubular carriers have been furnished in this way with unit doses of reagent, the upper end seal cover 46 is closed and the various unit carriers can thereafter be fed into a a sealed air-tight cassette 67 of, for example, the type shown in FIG. 6. Provided in the wall of the tubular carriers 43 are diametrically opposed iron wires 47 or other magnetic material, as a result of which the unit carriers after being introduced into a reaction tube, on an analysis machine can be caused to move up and down in the basic solution in the reaction tube by means of electromagnetic coils surrounding said reagent tubes, so that the reagent in the tubular carrier is caused to be dissolved in the basic solution. Obviously the covers 44 and 46 of the tubular carrier 43 must be opened before said unit is lowered into the reagent tube in which the reaction is to take place.

FIG. 5 shows a carrier means comprising the carrier means and unit dose of FIG. 1 or 2 and the tubular carrier 43 of FIG. 4, the unit dose and carrier of FIGS. 1 and 2 having been lowered into a tubular carrier 53, the wall of which is provided with iron wires 47.

The cassette 67 shown in FIG. 6 with the carrier bodies 43 arranged in it is provided with a sealed mouth 68 adapted for fitting of a nozzle (not shown) for breaking the seal for dispensing of the composite micro-quantity reagent dosage unit for performing an analytical procedure. In the cassette there is a movable end wall 70, urged by springs 69 toward discharge mouth 68 to ensure discharge of carrier elements 43 from the mouth 68 when the mouth is unsealed.

The cassette 67 may be filled with a protective atmosphere, for example nitrogen gas in a dry air or ethylene oxide atmosphere.

FIGS. 1–6 also show the device for production of reagent units according to the invention, as also the method for production of such reagent units.

Although the invention has been described with reference to some of its embodiments, it can nevertheless be arbitrarily varied within the scope of the subsequent claims.

What is claimed is:

1. A prefabricated micro-quantity reagent dosage unit for use in the course of an analytical procedure involving reaction of a chemical reagent with a reaction mixture to be analyzed, said unit comprising a chemical reagent of predetermined volume, a tube open at both its ends for carrying therewithin said chemical reagent of predetermined volume, sealing means cooperating with said tube for sealingly containing said reagent therein during storage, and a magnetizable material embedded in the wall of said tube to facilitate handling of said tube and for effecting movement of the tube, and thus the reagent carried thereby, when subjected to said reaction mixture, said tube, said reagent, said sealing means and said magnetizable material comprising a composite structure adapted for storage, transfer and use in a single analytical procedure under action of magnetic forces adapted to be applied to said magnetizable material.

2. The reagent dosage unit of claim 1, wherein said reagent is formulated with viscosity raising substances selected from the group consisting of agar-agar, pectins, gelatin and cellulose derivatives to form a gel.

3. The reagent dosage unit of claim 1, wherein the reagent is deposited upon a plastic band inserted and enclosed within the carrier tube.

4. The reagent dosage unit of claim 1, wherein said reagent has a volume of less than 30 $\mu$l.

5. The unit according to claim 1, wherein the tube is of plastic material and said sealing means comprises end closures for the tube.

6. The unit according to claim 1, incorporated in an airtight cassette adapted for ready dispensation of unit dosage elements in sequence into said reaction mixture.

* * * * *